Figure 1:
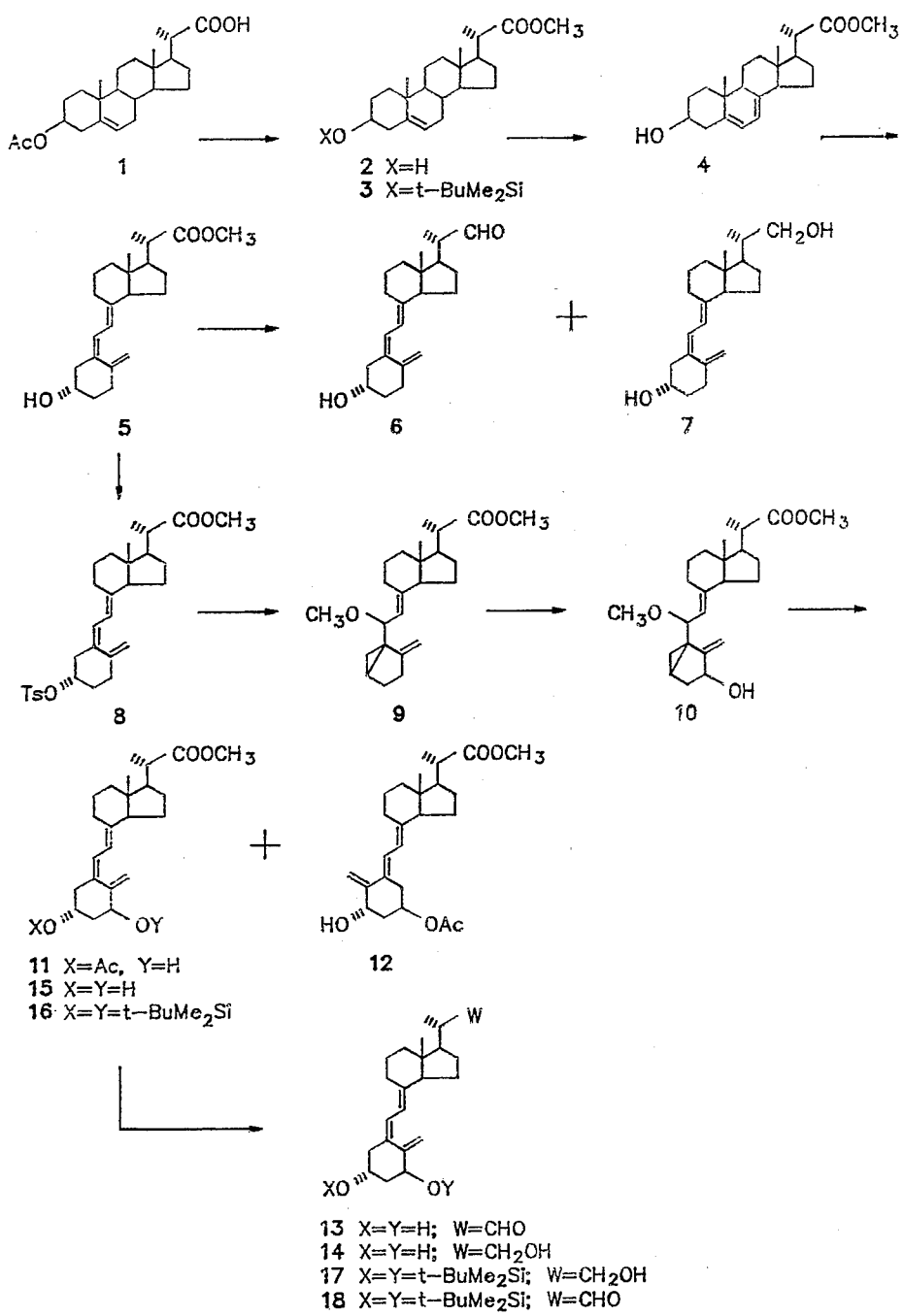
Figure 2:
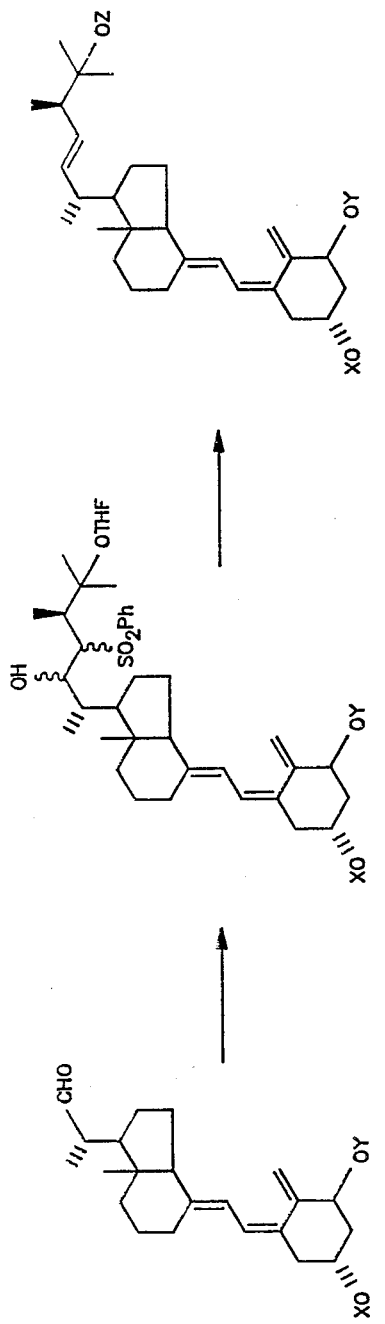
Figure 3:
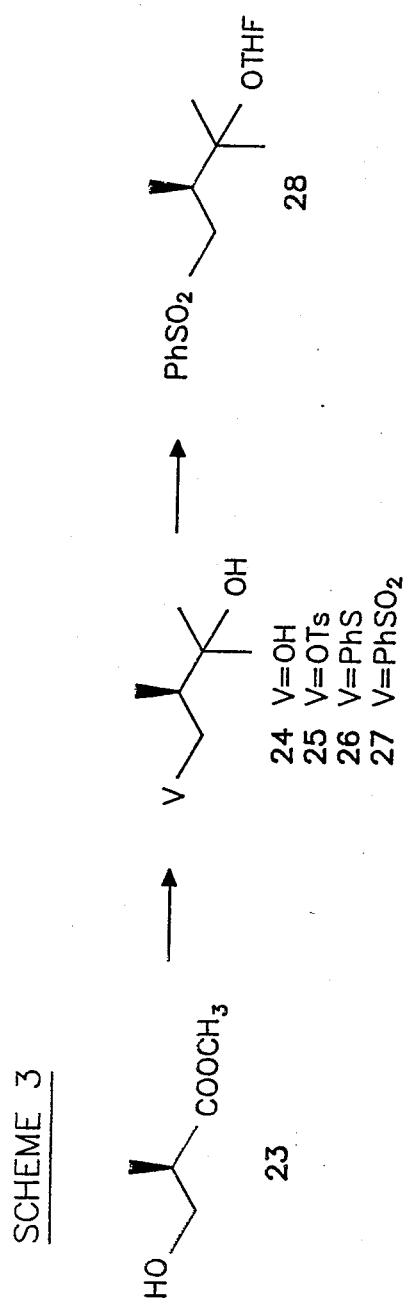

United States Patent [19]

DeLuca et al.

[11] Patent Number: 4,847,012

[45] Date of Patent: Jul. 11, 1989

[54] VITAMIN D RELATED COMPOUNDS AND PROCESSES FOR THEIR PREPARATION

[75] Inventors: Hector F. DeLuca, Deerfield; Heinrich K. Schnoes, Madison, both of Wis.; Andrzej Kutner, Warsaw, Poland; Kato L. Perlman, Madison, Wis.; Rafal R. Sicinski, Warsaw, Poland; Mary E. Phelps, Stoughton, Wis.

[73] Assignee: Wisconsin Alumni Research Foundation, Madison, Wis.

[21] Appl. No.: 188,334

[22] Filed: Apr. 29, 1988

[51] Int. Cl.[4] .............................................. C07J 9/00
[52] U.S. Cl. ................................................. 260/397.2
[58] Field of Search ...................... 260/397.2; 514/167

[56] References Cited

FOREIGN PATENT DOCUMENTS 251141 11/1987 German Democratic Rep. .................................. 260/397.2

Primary Examiner—Douglas W. Robinson
Assistant Examiner—Joseph A. Lipovsky
Attorney, Agent, or Firm—Andrus, Sceales, Starke & Sawall

[57] ABSTRACT

The invention relates to a method for preparing vitamin D-related compounds and to certain intermediate compounds in such process. The intermediate compounds are characterized by an aldehyde or ester in the C-22 position in the side chain. The presence of such groups permit facile side chain additions for the preparation of vitamin D derivatives.

17 Claims, 3 Drawing Sheets

SCHEME 1

VITAMIN D RELATED COMPOUNDS AND PROCESSES FOR THEIR PREPARATION

The invention described herein was made in the course of work supported by a grant or award from the Department of Health and Human Services. The Government has certain rights in this invention.

This invention involves vitamin D related compounds. More specifically, the invention relates to intermediates that are useful in the production of biologically-active metabolites or of variants of vitamin D, and to processes for the production of these intermediates, and their conversion to the desired vitamin D compounds.

BACKGROUND OF THE INVENTION

The D vitamins are important agents for the control of calcium and phosphate metabolism in animals and humans. They have long been used as dietary supplements and in clinical practice to assure proper bone growth and development. It is now known that the in vivo activity of these vitamins is dependent on hydroxylated forms of the vitamin. Especially important in this context are 1α-hydroxylated vitamin D derivatives. Further, it has also been learned that side chain structures are important in effecting vitamin D's biological activity.

Many processes for the preparation of vitamin D compounds have been reported in the literature. Among them are processes employing steroid aldehydes as precursors for the synthesis of vitamin D metabolites, or of side chain modified analogs [see, for example, Yamada et al., Tetrahedron Letters, 22, 2591–94 (1981); Sardina, et al., Tetrahedron Letters 24, 4477–4480 (1983); Morzycki et al., J. Org. Chem. 49, 2148 (1984); Sai et al., Chem Pharm. Bull. 34, 4508–15 (1986)]. After coupling the steroid aldehyde with a selected side chain fragment, one can then create the vitamin D triene system, and by means of regio- and stereoselective 1-alpha-hydroxylation produce the resulting 1-alpha-hydroxyvitamin. This approach involves a multi-step generation of the triene system, a process which together with the 1-alpha-hydroxylation sequence, must be repeated every time a new analog is to be synthesized.

Likewise, certain side chain alcohols, aldehydes or esters, containing a vitamin D nucleus, have been used for the preparation of vitamin D3-derived metabolites or analogs by attachment of a side chain residue via Grignard-type reactions [U.S. Pat. No. 4,512,925; Andrews et al., J. Org. Chem. 51, 4819–4828 (1986)].

SUMMARY OF THE INVENTION

The present invention is directed to a process for the preparation of biologically active vitamin D metabolites or analogs, using vitamin D aldehyde derivatives as the general precursors for the generation of the desired side chain structure. The novel vitamin D-aldehydes of this invention allow for the preparation of useful vitamin D compounds, bearing many different side chains, from the same precursor, thus obviating the need for the repetitive and laborious generation of the 1-hydroxylated-triene system inherent in the older methods of synthesis from steroid precursors.

One aspect of the invention is to provide C-22-aldehyde and C-22-ester compounds of the following formula

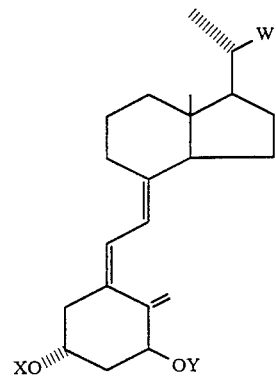

where X and Y, which may be the same or different, are selected from the group consisting of hydrogen and a hydroxy-protecting group, and where W is selected from the group consisting of CHO, COO-alkyl and COO-aryl). As used in the description and in the claims, the term "hydroxy-protecting group" refers to any group commonly used for the protection of hydroxy functions during subsequent reactions, including, for example, acyl or alkylsilyl groups, or alkoxyalkyl groups, such as methoxymethyl, ethoxymethyl, methoxyethyoxymethyl, tetrahydrofuranyl or tetrahydropyranyl. A "protected-hydroxy" is a hydroxy function derivatized by one of the above groupings. "Acyl" represents an alkanoyl group of 1 to 6 carbons in all isomeric forms, or a benzoyl- or substituted benzoyl group where the substituents may be nitro, halo or alkyl. "Alkyl" represents a straight-chain or branched hydrocarbon radical of 1 to 10 carbons in all its isomeric forms, and "aryl" is a phenyl or benzyl group, or an alkyl-, halo- or nitro-substituted phenyl or benzyl group.

These novel compounds are the key intermediates for the preparation of biologically active vitamin D metabolites or analogs according to the process of this invention. For example, the C-22-aldehydes having the formula shown above (where W=CHO), can be used for the convenient preparation of metabolites of the vitamin D2 series or side chain analogs thereof, by attachment of the appropriate side chain residue.

Such use is another aspect of this invention. The side chain attachment process is characterized by the reaction of a 22-aldehyde intermediate of the general structure shown above, with a sulfone-derivative of the general formula,

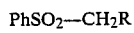

PhSO2—CH2R where Ph is a phenyl or an alkyl-substituted-phenyl group and R is selected from the group consisting of an alkyl or substituted alkyl radical, where the substituents are selected from the group consisting of hydroxy, protected hydroxy, and fluorine and any combination thereof.

Such phenylsulfone synthons are readily prepared, and have been used in a variety of organic synthetic processes [see P.D. Magnus, Tetrahedron 33, 2019 (1976)].

The coupling reaction, conducted in a basic medium, between the above aldehyde and sulfone derivatives yields a condensation product having the formula,

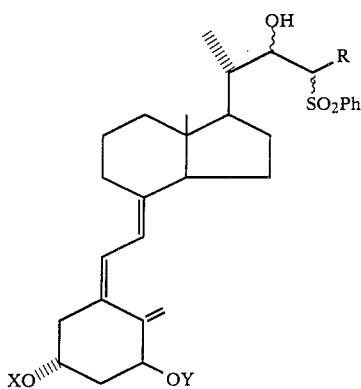

which is then subjected to reduction so as to provide vitamin D derivatives of the general formula,

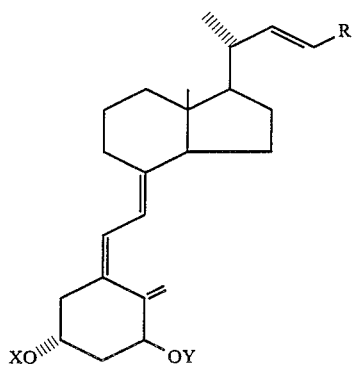

where R, X and Y represent the groupings defined above. Upon removal of hydroxy-protecting groups (if any) by standard methods well known in the art, the desired vitamin D metabolite or analog, characterized by a vitamin $D_2$-type trans-unsaturated side chain is obtained. The reductive removal of the hydroxy and phenylsulfonyl substituents can be effected by treatment with metal amalgams (e.g. Na, Al, Zn-amalgams), or by related dissolving metal reduction processes. Both the 22-hydroxy compound as well as the corresponding acylated derivatives can be reduced under these conditions. It is readily apparent that by suitable variation of R in the phenylsulfone derivative used in the above coupling process, a range of different vitamin D compounds can be produced. The side chain residue R can be any alkyl or hydroxy-alkyl group as previously defined. Preferred side chain sulfone units are those compounds in which the residue R is an alkyl or hydroxyalkyl radical, such as methyl, ethyl, propyl or higher straight-chain or branched homologs as represented by the following structures:

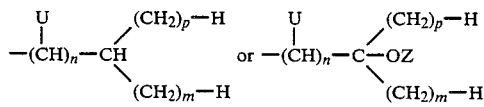

where U represents hydrogen, hydroxy, protected-hydroxy or a hydrocarbon radical of from 1 to 4 carbons, and where p, m, and n are integers having the values of 1 to 5, and where Z represents hydrogen or a hydroxy-protecting group. Specific examples of such preferred groupings are the compounds where R is an alkyl group, such as 2-methylpropyl, 3-methyl-2-butyl, 2-methylbutyl, 3-methylbutyl, 3-methylpentyl, 4-methylpentyl, 2-ethylbutyl, etc, or a hydroxy-substituted hydrocarbon radical such as, 2-hydroxy-2-methylpropyl, 3-hydroxy-3-methyl-2-butyl, 1,2-dihyroxy-2-methylpropyl, 2,3-dihydroxy-2-methylpropyl, 2-hydroxy-2-methylbutyl, 3-hydroxy-3-methylbutyl. Additionally, R can be a radical of the above type in which one or more hydrogen atoms are replaced by fluorine atoms, such as 1-fluoro- or 1,1-difluoro-2-hydroxy-2-methylpropyl, 2-hydroxy2-trifluoromethylpropyl or 2-hydroxy-2,2-ditrifluoromethylethyl, and any hydroxy groups present can be protected by the general hydroxy-protecting groups defined above, or, if adjacent, by isopropylidene groups.

Such phenylsulfone derivatives of the general structure $PhSO_2CH_2R$ can be prepared conveniently by several known procedures, e.g. according to the general sequence below:

$$V-CH_2R \rightarrow PhS-CH_2R \rightarrow PhSO_2CH_2R$$

in which the substitutent V in the starting material, V—$CH_2$—R, represents a leaving group, such as bromide, chloride, iodide, or a tosyloxy or mesyloxy group, which is displaced by reaction with thiophenol anion to provide the sulfide PhS—$CH_2$R, which in turn is oxidized to the sulfone product. Any free hydroxy groups that may be present in the radical R can then be derivatized with a hydroxy-protecting group according to established methods.

Importantly, the present invention permits the triene C-22-aldehyde or C-22-ester compounds to be prepared as stable intermediates, which can be selectively reacted to permit side chain syntheses.

The objects of the invention therefore include providing such intermediates as well as a process for their use in the preparation of vitamin D metabolites and [vitamin]analogs varying in side chain structure. Still other objects and advantages of the present invention will be apparent from the following description which, it should be understood, is intended to be illustrative only of the invention and not limiting of the appended claims.

SPECIFIC DESCRIPTIVE EXAMPLE OF THE PROCESS

A better understanding of the invention can be achieved by referring to the following specific description in conjunction with the appended process schemes, in both of which identical compounds are referred to by identical numbers.

A. Materials and Equipment

3β-Acetoxy-22,23,-bisnor-5-cholenic acid (1) was purchased from Steraloids (Wilton, N.H.). All other chemicals were of the best quality from commercially available sources. Solvents were purified by standard methods.

Thin-layer chromatography (TLC) was performed using precoated aluminum silica gel sheets with UV indicator from EM Science (Gibbstown, N.J.). Solvent systems used: A: chloroformethanol 85:15 (v/v); B: hexane-ethyl acetate 1:1 and C: hexane-ethyl acetate 3:1.

High-performance liquid chromatography (HPLC) was performed using a Waters Associates liquid chromatograph equipped with a Model 6000A solvent delivery system, a Model 6 UK Universal injector and a Model 450 variable wavelength detector. Zorbax-Sil (Phenomenex) columns (6.2 mm×25 cm and 10 mm×25 cm) were used. Solvent systems: A: 3% 2-propanol in hexane; B: 2% 2-propanol in hexane; C: 6% 2-propanol in hexane; D: 10% 2-propanol in hexane; E: 20% 2-propanol in hexane. Silica gel Sep-Pak (Waters Associates) cartridges were used for the prefiltration of HPLC samples.

Electron impact mass spectra (MS) were recorded at 70 eV with Kratos MS-50 TC Mass Spectrometer equipped with Kratos DS-55 Data System.

Ultraviolet (UV) absorption spectra were recorded with a Hitachi Model 60-100 UV-Vis spectrophotometer.

Infrared spectra were recorded on a Nicolet MX-1 FT-IR spectrometer using films of oily substances or carbon tetrachloride solutions.

Proton magnetic resonance spectra ($^1$H-NMR) were taken with a Bruker WH-270 FT spectrometer in $CDCl_3$ solutions containing tetramethylsilane (TMS) as internal standard.

B. Synthesis of C-22-Esters and Aldehydes (Compounds 11, 13, 15, 16 and 18; Scheme 1)

Compound (1) (10 g) was dissolved in 420 mL of 5% KOH in methanol and the solution was stirred at ambient temperature for 15 min until none of the starting material was detected by TLC (solvent system A). To this solution, 160 mL of 10% sulfuric acid in methanol was added dropwise with stirring and the resulting suspension was diluted with 400 mL of 1% sulfuric acid in methanol. The mixture was heated under reflux for 48 h to complete the esterification (TLC, solvent system A). Compound (2) (the ester) was extracted with ethyl acetate. The organic phase was washed with 5% $NaHCO_3$, saturated NaCl and dried over magnesium sulfate. The product, compound (2), (9.0 g, 88%) was used for the next step without further purification.

To a solution of compound (2) (4.4 g, 12 mmol) in 135 mL of dry dimethylformamide (DMF) was added imidazole (3.6 g, 52.8 mmol), followed by tert-butyldimethylsilyl chloride (4.0 g, 26.4 mmol). The solution was stirred at room temperature for 5 min until the bulky precipitate was formed and then stirring was continued for additional 15 min. The reaction mixture was extracted with hexane (400 mL), washed with water, saturated NaCl solution, and dried over magnesium sulfate. Evaporation of the solvent provided TLC pure (solvent system B) product, compound (3) (5.3 g, 91%), that was used for the next step without further purification. An analytical sample was obtained by flash chromatography using 2% ethyl acetate in hexane.

A mixture of compound (3) (1.0 g, 2.1 mmol), dibromantin (0.42 g, 1.5 mmol) and anhydrous sodium bicarbonate (0.91 g, 10 mmol) in 20 mL of hexane was heated under reflux in a nitrogen atmosphere for 30 min until no starting compound (3) was detected (TLC, system C). The precipitate was filtered off and the solution dried down under reduced pressure. The residue was redissolved in 5 mL of anhydrous THF, tetrabutylammonium bromide (0.06 g, 0.19 mmol) was added, and the mixture stirred at room temperature for 30 min under nitrogen. A solution of tetrabutylammonium fluoride (10 mL, 1M in THF) was then added, followed by 0.7 mL of s-collidine, and the mixture was stirred under nitrogen at room temperature for 1 h. Another 5 mL of tetrabutylammonium fluoride solution was added and stirring was continued for 3 h. Ether (50 mL) was dded and the organic phase was washed with water, cold 1 N HCl, 10% $NaHCO_3$ and dried over anhydrous magnesium sulfate. The product, compound (4), dissolved in benzene solvent, was chromatographed on silica gel 70-230 mesh (30 g). Compound (4) (0.44 g, 58%) was eluted using ethyl acetate in hexane. An analytical sample was obtained by HPLC (system A, $R_V$77 mL): IR (film) 1737, 1604, 1495, 1082, 1030 $cm^{-1}$; UV (3% 2-propanol in hexane) $\lambda_{max}$262 nm ($\epsilon$7,000), $\lambda_{max}$272 nm ($\epsilon$9,800), $\lambda_{max}$282 nm ($\epsilon$10,500), $\lambda_{max}$293 ($\epsilon$6,000); $^1$H NMR ($CDCl_3$)$\epsilon$6 0.54 (3H, s, 18—$CH_3$), 0.94 (3H, s, 19—$CH_3$), 1.22 (3H, d, J=6 Hz, 2—$CH_3$), 3.6 (1H, m, 3—H), 3.68 (3H, s, $CO_2CH_3$), 5.42 (1H, m, 6—H), 5.58 (1H, m, 7—H); MS m/z (relative intensity) 358 (61), 340 (12), 325 (100), 299 (68), 271 (7), 253 (17), 237 (26), 211 (27), 143 (72), 119 (35).

A solution of compound (4) (830 mg, 2.3 mmol) in 350 mL of benzene-ethyl ether, 1:4 (v/v) was irradiated with stirring under nitrogen in a water-cooled quartz immersion well equipped with a nitrogen bubbler and a Vycor filter using Hanovia 608A36 medium-pressure UV lamp for 40 min (4×10 min). The reaction was monitored by HPLC using 2% 2-propanol in hexane at 265 nm. The solution was dried down under reduced pressure, redissolved in 100 mL of absolute ethanol and heated under reflux in a nitrogen atmosphere for 3 h. Then the solution was concentrated, redissolved in 1 mL of 10% ethyl acetate in hexane and chromatographed on silica gel 70-230 mesh (30 g). Compound (5) (298 mg, 36%) was eluted using a mixture of 15% ethyl acetate in hexane. An analytical sample was obtained by HPLC (system B, $R_V$94 mL): IR (film) 1738 $cm^{-1}$; UV (EtOH) $\lambda_{max}$ 264 nm, $\lambda_{min}$228 nm; $^1$H NMR ($CDCl_3$)$\delta$6, 0.56 (3H, s, 18—$CH_3$), 1.20 (3H, d, J=7 Hz, 21—$CH_3$), 3.66 (3H, s, $CO_2CH_3$), 3.95 (1H, m, 3—H), 4.80 (1H, d, J=1.2 Hz, 19Z—H), 5.05 (1H, d, J=1.2 Hz, 19E—H), 6.03 (1H, d, J=11 Hz, 7—H), 6.23 (1H, d, J=11 Hz, 6—H); MS m/z (relative intensity), M$^+$358 (45), 340 (9), 325 (45), 299 (22), 253 (19), 237 (18), 136 (60), 118 (100).

A solution of compound (5) (10 mg, 0.028 mmol) in 5 mL of dry toluene was cooled under nitrogen to −70° C. in a dry ice-acetone bath. To this solution, diisobutylaluminum hydride (DIBAL-H, 50 µL, 25% solution in toluene, 0.088 mmol) was added dropwise with stirring. The reaction mixture was stirred at −70° C. for 10 min and then methanol (2 mL) was slowly added. The mixture was allowed to warm up to room temperature, diluted with ethyl ether and washed with 5% HCl, 5% $NaHCO_3$, water, saturated NaCl and dried over anhydrous magnesium sulfate. Silica gel chromatography (15% ethyl acetate in hexane) afforded compound (6) (4.9 mg, 54%), with the following spectral data: MS: 328 (M$^+$, 29), 310 (5), 295 (31), 269 (11), 253 (6), 136 (47), 118 (86), 29 (100); $^1$H—NMR ($CDCl_3$)$\delta$: 0.59 (3H, s, 18—$CH_3$), 1.14 (3H, d, J=7 Hz, 21—CH3), 4.0 (1H, m, 3—H), 4.81 (1H, d, J=1.2 Hz, 19E—H), 5.05 (1H, d, J=1.2 Hz, 19Z—H), 6.05 (1H, d, J=11 Hz, 7—H), 6.23 (1H, d, J=11 Hz, 6—H), 9.58 (1H, d, J=3.8 Hz, 22—H).

Further elution of the silica gel column with 5% 2-propanol in hexane yielded the C-22-alcohol, compound (7) (2.7 mg, 29%).

Compound (5) was converted into compound (8) by using p-toluenesulfonyl chloride in pyridine at 4° C. for 20 h. Compound (8) (102 mg, 0.2 mmol) dissolved in 2 mL of anhydrous dichloromethane was added to the methanol solution (15 mL) of anhydrous potassium bicarbonate (250 mg) with stirring at 55° C. The mixture was stirred under nitrogen at 55° C. for 24 h. The solvents were then removed under reduced pressure and the residue extracted with ether. The organic phase was washed with water and dried over anhydrous magnesium sulfate. The product, compound (9), was purified by silica gel chromatography using 20% ethyl acetate in hexane (50 mg, 68%).

Tert-butyl hydroperoxide (112 μL, 3.0M solution in toluene, 0.34 mmol) was added to a suspension of selenium dioxide (9 mg, 0.8 mmol) in 2 mL of dry methylene chloride. The mixture was stirred at room temperature under nitrogen until a clear solution was formed. Anhydrous pyridine (12 μL, 0.15 mmol) was then added followed by compound (9) (50 mg) dissolved in 2 mL of anhydrous dichloromethane. The mixture was stirred under nitrogen for 30 min. Cold 10% sodium bicarbonate (2 mL) was added and the mixture extracted with ether. The organic phase was washed with cold 10% sodium bicarbonate, ice water and dried over anhydrous magnesium sulfate. Silica gel chromatography (10-20% ethyl acetate in hexane) afforded 12.5 mg of compound (10). The product was then immediately dissolved in 0.5 mL of glacial acetic acid and the solution was heated at 55° C. with stirring under nitrogen for 15 min. The reaction mixture was poured over ice, extracted with ether and washed with ice-cold saturated sodium bicarbonate. The combined ether extracts were washed with water and dried over anhydrous magnesium sulfate. Analytical samples of (5Z,7E) and (5E,7E) isomers, (11) and (12), respectively were obtained by preparative HPLC in a ratio of 2.5:1.

Compound 11: HPLC, $R_V$68 mL; UV (EtOH) $\lambda_{max}$264 nm, $\lambda_{min}$227 nm, A264/A227=2.07; $^1$H NMR (CDCl$_3$)δ0.56 (3H, s, 18—CH$_3$), 1.20 (3H, d, J=6.5 Hz, 21—CH$_3$), 2.04 (3H, s, 3β—OAc), 3.66 (3H, s, 22—CO$_2$CH$_3$), 4.4 (1H, m, 3—H), 5.2(1H, m, 3—H), 5.01 (1H, br s, 19E—H), 5.34 (1H, br s, 19Z—H), 6.01 (1H, d, J=10 Hz, 7—H), 6.33 (1H, d, J=10 Hz, 6—H); MS m/z (relative intensity), 416 (M+, 4), 356 (100), 338 (21), 251 (13), 134 (95). Compound 12: HPLC, $R_V$78 ml; UV (EtOH)$\lambda_{max}$267 nm, $\lambda_{min}$227 nm, A267/A227=3.51; $^1$H NMR (CDCl$_3$)δ0.56 (3H, s, 18—CH$_3$), 1.20 (3H, d, J=6.5 Hz, 21—CH$_3$), 2.04 (3H, s, 3β—OAc), 3.66 (3H, s, 22—CO$_2$CH$_3$), 4.5 (1H, m, 1—H), 5.3 (1H, m 3—H), 4.99(1H, m, 3-H), 4.99 (1H, br s, 19E—H), 5.13 (1H, br s, 19Z—H), 5.81 (1H, d, J=10 Hz, 7—H), 6.56 (1H, d, J=10 Hz, 6—H).

For large scale preparations, isomers (11) and (12) can also be effectively and advantageously separated by the maleic anhydride procedure described in U.S. Pat. No. 4,554,106.

Diisobutylaluminumhydride (15 μL, 1.5M solution toluene) was added with stirring to a solution of compound (11) (2 mg) in 0.5 mL of anhydrous toluene at −70° C. under nitrogen. The mixture was stirred at −70° C. for 10 min and 0.2 mL of methanol was slowly added to decompose the organometallic complex. The mixture was warmed up to room temperature and extracted with ethyl ether. The organic phase was washed with water and dried over anhydrous magnesium sulfate. Preparative HPLC, using a solvent system E afforded compound (13) and compound (14). Compound (13) gave the following spectral data: 344 (M+, 22), 326 (13), 311 (2), 285 (4), 269 (4), 152 (29), 134 (100); $^1$H—NMR (CDCl$_3$)δ, 0.59 (3H, s, 18—CH$_3$), 1.15 (3H, d, J=7 Hz, 21—CH$_3$), 4.2 (1H, m, 3—H), 4.99(1H, d, J=1.2 Hz, 19Z—H), 5.31 (1H, d, J=1.2 Hz, 19E—H), 6.02 (1H, d, J=11 Hz, 7—H), 6.36 (1H, d, J=11 Hz, 6—H), 9.56 (1H, d, J=4 Hz, 22—H).

A 0.1N solution of KOH in methanol (10 mL) was added to a stirred solution of compound (11) (100 mg, 0.24 mmol) in ethyl ether (10 mL). The resulting solution was stirred at room temperature for 90 min until no starting material was detected by TLC (solvent system B). Compound (15) was isolated by standard extraction procedure (ethyl acetate, saturated NaCl, anhydrous magnesium sulfate) to give colorless oil (86.2 mg, 96%).

A mixture of imidazole (250 mg, 3.6 mmol) and tert-butyldimethylsilyl chloride (250 mg, 1.6 mmol) in DMF (2 mL) was added to a stirred solution of compound (15) (86.2 mg, 0.23 mmol) in 4 mL of dimethylformamide. The resulting homogenous mixture was stirred for 15 min at 55° C. until no starting material was detected by TLC((solvent system B). The product was isolated by hexane extraction of the reaction mixture. Organic extract was washed with brine and dried over anhydrous magnesium sulfate. Hexane solution of the crude product was filtered through silica gel Sep-Pak cartridge to give compound (16) (136 mg, 98%). IR (film) 2974, 2930, 1736, 1447, 1286, 1258, 1150, 1085 cm$^{-1}$; UV (hexane), $\lambda_{max}$264 nm, $\lambda_{min}$227 nm, A264/A227=1.91; $^1$H NMR (CDCl$_3$), δ0.07 [12H, s, Si(CH$_3$)$_2$], 0.55 (3H, s, 18—CH$_3$), 0.86 [18H, s, C(CH$_3$)3], 1.20 (3H, d, J=6.8 Hz, 21—CH3), 3.65 (3H, s, 0—CH$_3$), 4.18 (1H, m, 3-H), 4.36 (1, m, 1—H), 4.84 (1H, d, J=1.2 Hz, 19Z—H), 5.16 (1H, d, J=1.2 Hz, 19E—H), 5.96 (1H, d, J=11.2 Hz, 7—H), 6.19 (1H, d, J=11.2 Hz, 6—H); MS m/z (intensities normalized to m/e 248) 602 (M+, 10), 470 (59), 413 (7), 338 (10), 248 (100).

Lithium aluminum hydride (25 mg, 0.65 mmol) was added to a stirred solution of compound (16) (136.2 mg, 0.23 mmol) in anhydrous THF (5 mL) under argon at 0° C. The suspension was stirred for 15 min at 0° C. and the excess of lithium aluminum hydride was decomposed by the dropwise addition of 10% water in THF. The suspension was diluted with 10 mL of THF and the stirring was continued for an additional 15 min at room temperature. The product was isolated by the standard extraction with ethyl acetate. Compound (17) was obtained as a colorless oil (118.4 mg) in 91% yield. IR (film) 3450, 2952, 2886, 1447, 1258, 1105, 1085, 834 cm$^{-1}$; UV (EtOH)$\lambda_{max}$264 nm, $\lambda_{min}$227 nm, A264/A227=1.57; $^1$H NMR (CDCl$_3$)δ0.00 (12H, s, Si—CH$_3$), 0.53 (3H, s, 18—CH ), 0.85 [18H, s, Si-C(CH$_3$)$_3$], 1.04 (3H, d, J=6.4 Hz, 21—CH ), 3.37 and 3.63 (1H and 1H, each m, 22—CH$_2$), 4.17 (1H, m, 3—H), 4.35 (1H, m, 1—H), 4.84 (1H, br s, 19Z—H), 5.16 (1H, br s, 19E—H), 6.00 (1H, d, J=12.2 Hz, 7—H), 6.21 (1H, d, J=12.2 Hz, 6—H); MS M/z (intensities normalized to m/z 248), 574(M+, 17), 442(67), 383(11), 308(17), 248 (100).

A solution of oxalyl chloride (30μL, 0.34 mmol) in 0.5 mL of dichloromethane was added dropwise to a stirred solution of DMSO (50 μL, 0.7 mmol) in 3 mL of dichloromethane at −60° C. under nitrogen. The resulting solution was stirred at −60° C. for 10 min and the solution of compound (17) (27 mg, 0.05 mmol) in 1 mL of dichloromethane was slowly added. The mixture was stirred for 30 min at −60° C. Then 0.2 mL of triethylamine was added and the solution was stirred for another 5 min. The product, compound (18), was extracted with ethyl ether and the organic extract was washed with saturated NaCl and dried over anhydrous magnesium sulfate. Silica gel Sep-Pak filtration afforded TLC pure product (17 mg, 62%). IR (film) 2954, 2929, 2884, 2857, 1727, 1472, 1375, 1256, 1085, 909, 880, 835 cm$^{-1}$; NMR (CHCl$_3$)$\delta$0.00 (12H, s, Si—CH$_3$), 0.60(3H, s, 18—CH$_3$), 0.88 [18H, s, Si—C(CH$_3$)$_3$], 1.11 (3H, d, J=6.9 Hz, 21—CH$_3$), 4.23 (1H, m, 3—H), 4.43(1H, m, 1—H), 4.93(1H, br s, 19Z—H), 5.19(1H, br s, 19E—H), 6.07(1H, d, J=10.0 Hz, 7—H), 6.26 (1H, d, J=10.0 Hz, 6—H), 9.54(1H, d, J=3 Hz, 22—H); UV (hexane)$\lambda_{max}$264 nm, $\lambda_{min}$227 nm, A264/A227=1.9; MS m/z (intensities relative to m/z 248) 572(M$^+$, 13), 440(53), 383(11), 308(14), 248(100); exact mass calculated for C$_{34}$H$_{60}$O$_3$Si$_2$572.4081, found 572.4117.

C. Side Chain Addition (Scheme 2)

To prepare the vitamin D compound (22) from a C-22-aldehyde precursor, a solution of 1,10-phenanthroline in THF was added as indicator to a 1.35M solution of n-BuLi in hexane (47 μL, 0.063 mmol) to get a red mixture. The mixture was cooled under argon to −76° C. and diisopropylamine (9.6 μL, 0.068 mmol) was added with stirring. The mixture was stirred for 20 min at −75° C. and then the solution of phenylsulfone compound (28) (see Scheme 3) (26.5 mg, 0.085 mmol) in 0.5 mL of anhydrous THF was added dropwise to get a brown-red clear solution. The mixture was stirred on acetone-dry ice bath for 30 min and the solution of C-22-aldehyde (18) (10 mg 0.017 mmol) in 0.7 mL of THF was added dropwise. Stirring was continued for 1.5 h, and then saturated solution of ammonium chloride was added at −75° C. to get the yellow solution. The reaction mixture was extracted with ethyl ether and the organic phase was washed with saturated NaCl. Silica gel flash chromatography (7 g, 230-400 mesh) with 1% ethyl acetate in hexane afforded the unreacted compound (18) (3.6 mg). Elution of the column with 10% ethyl acetate in hexane gave the desired vitamin hydroxy-sulfone adduct (19). Compound (19) was used for the next step without further purification. Further elution with the same solvent yielded unreacted sulfone (28).

A large excess of 5% sodium amalgam was added under nitrogen to a stirred solution of hydroxysulfone (19) (4.2 mg) in 1 mL of saturated methanol solution of anhydrous Na$_2$HPO$_4$ at 0° C. After 2 h, another portion of sodium amalgam was added followed by powdered anhydrous Na$_2$HPO$_4$. The reaction mixture was stirred for another 3 h, quenched with ice-cold water and extracted with ethyl ether. Silica gel Sep-Pak filtration with 1% ethyl acetate in hexane yielded compound (20) (1.95 mg, 55%).

Vitamin D analog (20) (0.95 mg) was dissolved in 100 μL of a 1% solution of pyridinium p-toluene sulfonate in methanol. The resulting solution was stirred at room temperature for 15 min and the product was extracted with ethyl ether. Organic extract was washed with saturated NaCl and dried over anhydrous magnesium sulfate to give analog (21) (0.8 mg, 95%). The product was used for the next step without further purification.

A solution of tetrabutylammonium fluoride in THF (20 μL, 1.1M) was added to the solution of analog (21) (640 μg) in 1 mL of anhydrous THF at 55° C. The mixture was stirred under nitrogen for 50 min and quenched with water. The mixture was extracted with ethyl ether and the organic extract washed with saturated NaCl. Analog (22) was obtained (337 μg, 81%) by preparative HPLC (Zorbax-Silica column, 6.2 mm×25 cm) with the solvent system D. IR (film) 3411, 1643, 1630, 971 cm$^{-1}$; UV (EtOH)$\lambda_{max}$264 nm, $\lambda_{min}$229 nm, A264/A229=1.57; $^1$H NMR (CHCl$_3$)$\delta$0.54 (3H, s, 18—CH$_3$), 0.97 (3H, d, J=6.9 Hz, 28—CH ), 1.01 (3H, d, J=6.6 Hz, 21—CH$_3$), 1.10 and 1.15 (3H and 3H, each s, 26—CH$_3$ and 27—CH ), 4.21 (1H, m, 3—H), 4.41 (1H, m, 1—H), 4.97 (1H, br s, 19Z—H), 5.29 (2H, m, 22H and 23—H), 5.31 (1H, br s, 19E—H), 5.99 (1H, d, J=11.2 Hz, 7—H), 6.35(1H, d, J=11.2 Hz, 6—H); MS m/z (relative intensity), 428 (3), 410 (9), 392 (10), 374 (3), 352 (8), 287 (2), 269 (6), 251 (6), 155 (11), 152 (10), 135 (28), 134 (33), 59 (100); exact mass calculated for C$_{28}$H$_{44}$O$_3$428.3290, found 428.3268.

D. Preparation of Side Chain Sulfone Group (Scheme 3)

A solution of known ester (23) (2.11 g, 17.9 mmol) in 8 mL of anhydrous THF was added dropwise to a stirred solution of methyl-magnesium bromide (30 mL, 2.7 mmol) under nitrogen at 0° C. The mixture was stirred at ambient temperature for 2 h and ice-cold diluted hydrochloric acid was slowly added. The mixture was extracted with ethyl ether and worked up by standard methods to give the diol (compound 24) as a colorless oil (1.2 g, 57%). The oil was dissolved in 5 mL of anhydrous pyridine and to this solution p-toluenesulfonyl chloride (2.34 g, 12.3 mmol) was added with stirring. The mixture was stirred for 16 h at 4° C. and quenched with ice-cold saturated NaHCO$_3$. The resulting suspension was stirred at room temperature for 30 min and extracted with ethyl ether. The extract was washed with water, water, saturated copper sulfate, water and saturated NaCl. Silica gel flash chromatography with 20% ethyl acetate in hexane gave a tosylate (compound 25) (2.14 g, 76%). Compound (25) (1.6 g, 5.9 mmol) was dissolved in 2 mL of anhydrous DMF and the solution was added to the stirred solution of thiophenol (0.7 g, 6.4 mmol) in 5 mL of anhydrous DMF. The mixture was stirred at room temperature overnight and ice water was added. The mixture was extracted with dichloromethane and worked up in the usual way. Silica gel flash chromatography with 10% ethyl acetate in hexane yielded compound (26), the sulfide (1.19 g, 95%). The product (1.1 g, 5.2 mmol) was dissolved in 15 mL of dichloromethane and to this solution 3-chloroperoxybenzoic acid (1.5 g, 8.7 mmol) was added with stirring. The mixture was stirred for 2 h at 0° C. until the yellow color of the mixture disappeared and a white precipitate was formed. Then the mixture was washed with NaHCO$_3$, sodium sulfite, and worked up by the usual method. Silica gel flash chromatography with 30% ethyl acetate in hexane gave the hydroxy sulfone compound (27) as a crystalline material (693 mg, 54%).

Pyridinium p-toluenesulfonate (10 mg) was added to the solution of the compound (27) in 1 mL of anhydrous dichloromethane followed by 0.2 mL of freshly distilled 2,3-dihydrofuran. The mixture was stirred overnight, diluted with dichloromethane and worked up in the usual way. Silica gel flash chromatography with 20% ethyl acetate in hexane gave a protected sulfone (compound 28) as a colorless oil.

It will be appreciated that while compound (28) is one sulfone, many other sulfones can be prepared with the sulfonyl group linked to any carbon chain of interest (with suitable protection on other groups) by analogous techniques. C.f. S. Yamada et al., Tet. Lett. 3347-3350 (1984). For example, starting with methyl (S)-2-methyl-3-hydroxypropionate (the epimer of compound 23), and using the above described reaction sequence, there is obtained (3S)-2,3-dimethyl-4-phenylsulfonyl-2-butanol (the methyl epimer of 27). Reaction of this alcohol with dihydropyran under standard conditions then gives the hydroxy-protected tetrahydropyranyl derivative. Similarly, by procedures entirely analogous to those described above, the known methyl 4-hydroxybutanoate is converted to 2-methyl-5-phenylsulfonyl-2-pentanol, or its hydroxy-protected derivatives. Known phenylsulfonyl derivatives can also be used as starting materials for side chain sulfone synthesis. For example, 3-phenylsulfonylpropionic acid, after esterification and subsequent Grignard reaction provides 2-methyl-3-phenyl sulfonyl-2-butanol (using MeMgBr in the Grignard step) or 3-ethyl-5-phenylsulfonyl-3-pentanol, or higher homologs (using EtMgBr or higher alkyl-MgBr for the Grignard reaction). Any such hydroxylated phenylsulfone units are readily converted to the corresponding hydroxy-protected forms by standard methods. Hydroxy-protection using tetrahydrofuranyl (THF), tetrahydropyranyl (THP), or the various alkylsilyl groupings provides derivatives suitable for the processes of this invention.

Non-hydroxylated phenylsulfone side chain units are, of course, prepared by methods entirely analogous to those described above, e.g. using alkylhalides or alkyl alcohols—where the alkyl group corresponds to the side chain structure desired—as readily available starting materials. All such phenylsulfonyl derivatives can serve as the side chain unit for coupling to the vitamin D C—22-aldehyde so as to produce a desired vitamin D compound or vitamin D analog.

We claim:

1. Compounds having the formula:

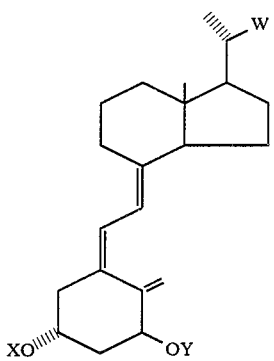

where X and Y, which may be the same or different, are each selected from the group consisting of hydrogen, and a hydroxy-protecting group, and where W is selected from the group consisting of CHO, COO-alkyl and COO-aryl.

2. The compounds of claim 1, wherein X and Y are hydrogen.

3. The compounds of claim 2 where W is CHO.

4. The compound of claim 2, where W is COOCH$_3$.

5. The compounds of claim 1, wherein X and Y are hydroxy-protecting groups

6. Compounds according to claim 5 where W is CHO

7. Compounds according to claim 3 where W is COOCH$_3$.

8. The compound of claim 1, wherein X and Y are t-butyl-dimethylsilyl, and W is CHO.

9. A compound of the formula:

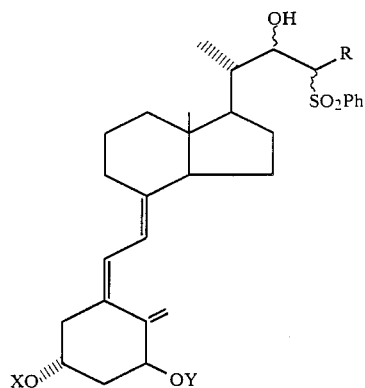

wherein R is selected from the group consisting of alkyl, hydroxylated alkyl, hydroxy-protected-hydroxylated alkyl, fluoro-substituted alkyl, fluoro-substituted hydroxylated alkyl and fluoro-substituted hydroxy-protected alkyl, and where X and Y, which may be the same or different, are each selected from the group consisting of hydrogen and a hydroxy-protecting group.

10. A method for preparing vitamin D compounds of the formula

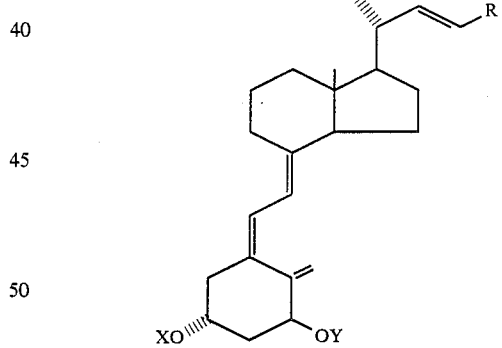

wherein R is selected from the group consisting of alkyl, hydroxylated alkyl, hydroxy-protected hydroxylated alkyl, fluoro-substituted alkyl, fluoro-substituted hydroxylated alkyl and fluoro-substituted hydroxy-protected alkyl, and where X and Y, which may be the same or different, are each selected from the group consisting of hydrogen and a hydroxy-protecting group, which comprises, treating a C-22-aldehyde compound of the formula

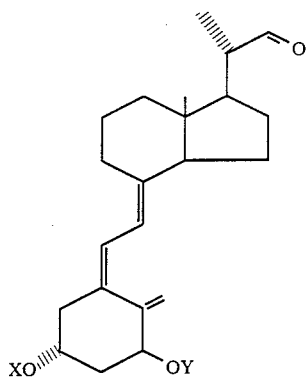

where X and Y are as defined above, with a phenylsulfone derivative of the formula

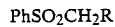

PhSO₂CH₂R wherein R is a group as defined above, in the presence of a strong base and an organic medium, whereby a hydroxy-sulfonyl adduct of the formula

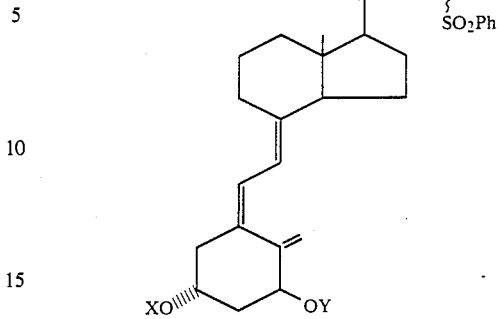

is obtained, wherein R, X and Y are as defined above, reducing said adduct to obtain the desired vitamin D compound, and, optionally, removing hydroxy-protecting groups.

11. The method of claim 10 where X and Y are hydroxyprotecting groups.

12. The method of claim 10 or of claim 11 where R is an alkyl group.

13. The method of claim 10 or of claim 11 where R is an hydroxylated alkyl group or a hydroxy-protected hydroxylated alkyl group.

14. The method of claim 10 or of claim 11 where R is a fluoro-substituted alkyl group.

15. The method of claim 10 or of claim 11 where R is a fluoro-substituted hydroxylated alkyl group, or a fluoro-substituted hydroxy-protected alkyl group.

16. The method of claim 11 where R is hydroxy-protected 3-methyl-3-hydroxy-2-butyl.

17. The method of claim 11 where R is hydroxy-protected 2-methyl-2-hydroxypropyl.

* * * * *